United States Patent
Fernandes

Patent Number: 5,839,898
Date of Patent: Nov. 24, 1998

[54] BALL RETAINER

[76] Inventor: Americo Fernandes, 3 Carmarthen Blvd., Winnipeg, Manitoba, Canada, R3P 0S3

[21] Appl. No.: 869,415

[22] Filed: Jun. 4, 1997

[51] Int. Cl.$^6$ ..................................................... A61C 8/00
[52] U.S. Cl. ............................................. 433/173; 433/172
[58] Field of Search ................................... 433/172, 173, 433/174, 175, 176

[56] References Cited

U.S. PATENT DOCUMENTS

| | | | |
|---|---|---|---|
| 3,618,212 | 11/1971 | Weissman | 433/174 |
| 4,431,416 | 2/1984 | Niznick | 433/174 |
| 4,793,808 | 12/1988 | Kirsch | 433/173 |
| 4,832,601 | 5/1989 | Linden | 433/173 |
| 4,907,969 | 3/1990 | Ward | 433/173 |
| 4,975,059 | 12/1990 | Sendax | 433/173 |
| 5,007,835 | 4/1991 | Valen | 433/174 |
| 5,071,350 | 12/1991 | Niznick | 433/173 |
| 5,073,110 | 12/1991 | Barbone | 433/173 |
| 5,211,561 | 5/1993 | Graub | 433/172 |
| 5,215,460 | 6/1993 | Perry | 433/173 |
| 5,520,540 | 5/1996 | Nardi et al. | 433/172 |
| 5,564,922 | 10/1996 | Rosa et al. | 433/173 |
| 5,597,306 | 1/1997 | Horlitz et al. | 433/173 |
| 5,695,334 | 12/1997 | Blacklock et al. | 433/173 |

*Primary Examiner*—John J. Wilson
*Attorney, Agent, or Firm*—Terrance L. Siemens

[57] ABSTRACT

A ball retainer for spanning and connecting an anchor osteointegrated into the jaw of a person and a dental prosthesis intended to be connected to the anchor. The ball retainer is formed in two separate parts. The first part has a column atop which is mounted a ball for engaging the prosthesis. The column has excess or sacrificial material. The second part has a hexagonal or otherwise non-circular shank for being inserted into and engaging the anchor, atop which is located a platform having a flat top surface. When being utilized in a particular prosthetic installation, excess material of the column is planed or otherwise removed to adjust height of the prosthesis from the anchor. Simultaneously, the cut is oriented appropriately for accommodating misalignment between the anchor and the intended orientation of the prosthesis. Preferably, the column is similar in diameter and cross sectional configuration to the platform of the anchoring member, and both are greater in diameter than the shank.

8 Claims, 1 Drawing Sheet

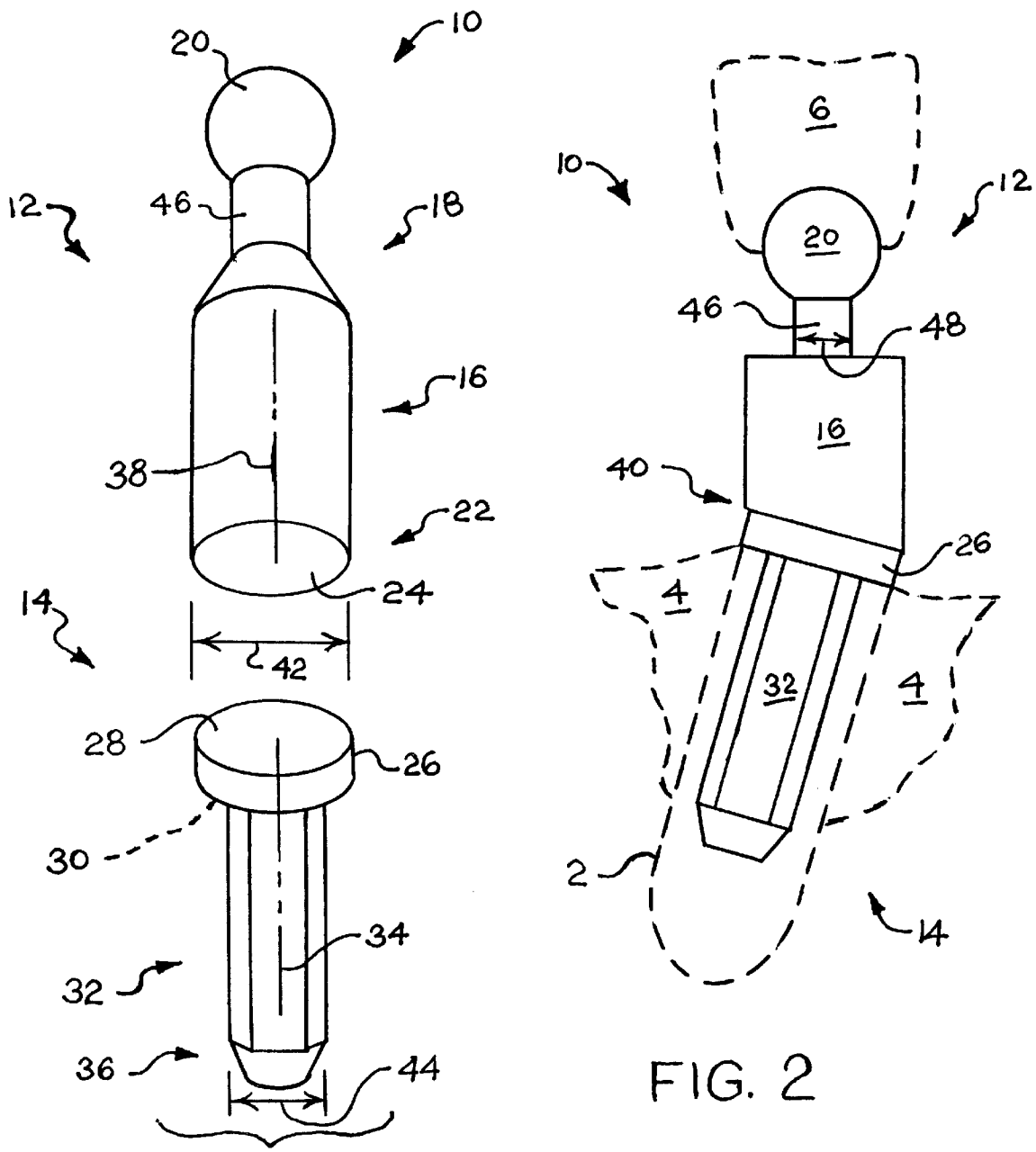

BALL RETAINER

BACKGROUND OF THE INVENTION

1. Field of the Invention

The present invention relates to a ball retainer for a dental implant. The ball retainer is an intermediate component employed to permanently mount a tooth prosthesis to an anchor permanently mounted in the jaw. The novel ball retainer is formed as a two part assembly enabling cutting or abrading of the base so that the ball may be mounted at a selected angle with respect to and a selected height above the anchor.

2. Description of the Prior Art

An individual prosthesis replacing a lost tooth may be anchored in the mouth of a patient at the site of the lost tooth. This procedure is conventionally performed in several steps. First, an anchor is placed in the jaw and allowed to osteointegrate to provide secure anchorage base for the prosthesis. The anchor is generally rectangular, having an external surface which is threaded or otherwise configured to engage bone tissue of the jaw. The exposed end of the anchor has an opening for receiving a prosthesis.

It is not feasible to place a tooth prosthesis directly into the opening of the anchor due to likely ensuing misalignment between the new tooth prosthesis and existing teeth or prostheses. This occurs because the anchor cannot be arbitrarily mounted in the jaw at an angle appropriate to support the new prosthesis at an orientation parallel to the existing teeth. Rather, the anchor must be oriented so as to engage existing bone tissue of the jaw as solidly as possible. The prosthesis must then be adjusted with respect to axial alignment with and height above the anchor.

Since height and alignment require two different adjustments, the dental fraternity has responded by providing an intermediate component which enables height above the anchor to be adjusted independently of axial alignment of the prosthesis to the anchor. This is the component which is the subject of the present invention.

Prior art intermediate components, which are generally called ball retainers, may have upwardly facing ball members, or alternatively may have upwardly facing socket members adapted to receive a ball formed in the prosthesis. U.S. Pat. No. 4,793,808, issued to Axel Kirsch on Dec. 27, 1988, illustrates one prior art intermediate component having an upwardly directed ball. However, unlike the present invention, this component threads to its anchor and also is not formed in two parts having opposed mating surfaces. Height adjustment cannot be made in the device of Kirsch by shortening one member to suit without sacrificing engagement threads.

U.S. Pat. No. 5,520,540, issued to Ezio Nardi et al. on May 28, 1996, and U.S. Pat. No. 5,597,306, issued to Sieglinde Horlitz et al. on Jan. 28, 1997, both show further examples of connecting devices wherein the device threads to the associated anchor, unlike the present invention. Neither of these prior art devices is formed in two mating parts providing opposed mating surfaces.

U.S. Pat. No. 4,832,601, issued to Harry A. Linden on May 23, 1989, describes an intermediate component having a hexagonal shaft. However, unlike the present invention, the device of Linden lacks an upwardly oriented ball and the two part construction of the novel device.

None of the above inventions and patents, taken either singly or in combination, is seen to describe the instant invention as claimed.

SUMMARY OF THE INVENTION

The present invention provides a ball retainer having a hexagonal shank for engaging a hexagonal opening formed in an anchor and an upwardly oriented ball. The novel ball retainer is formed in two parts having parallel facing surfaces. The ball retainer is formed in two mating parts. One part has the hexagonal shank and a platform mounted on the shank. The second part has the ball and a column having a bottom surface which will subsequently be adhered to the platform of the first part. The column is formed to a length excessive for most implant installations. This length provides sacrificial material which is abraded or cut away so that the final length of the column is appropriate for an individual installation of a prosthesis.

The cut or abrasion is made along a plane deemed appropriate to assure parallel orientation of the prosthesis relative to the existing teeth after final installation. One cut or modification to the novel ball retainer, if made at an appropriate planar orientation along the column, is sufficient to adjust both axial alignment of the ball with the anchor and overall height of the final assembled installation.

Provision of a member having sufficient excess material to enable height and alignment modification by removal of some material avoids risk of impairing connection to the anchor. If the threaded screw of a prior art connection device were planed away or otherwise remove to make height adjustments, the number of remaining threads could prove inadequate for secure attachment of the modified intermediate component to the anchor.

The assembly, both prior to modification for a particular application and after such modification, requires minimal fine detail, such as fine threads, which could be lost or distorted in a subsequent reproduction by molding or casting. Similar, extremely precise tolerances are not required. It is therefore easy for a dental laboratory technician to cast a final assembly for incorporation into the implant.

The member of the ball retainer which is modified is of relatively great diameter relative to other components except the mating part. This relationship allows a glued connection to be sufficiently large to assure a strong bond.

The ball of the ball retainer is supported on a narrow neck, so that a tooth prosthesis may be pivoted on the ball and inclined relative to axial alignment with the anchor.

Accordingly, it is a principal object of the invention to provide a ball retainer for a dental implant which may be adjusted for both overall height and for axial alignment with the anchor to which it will subsequently be connected.

It is another object of the invention that the ball retainer have a hexagonal connection shank, thereby being compatible with an anchor having a hexagonal opening for connection.

It is a further object of the invention that only one member be cut, planed, or otherwise reduced in dimension to make adjustment in both height and alignment.

Still another object of the invention is that the ball retainer have a prefabricated surface cooperating with the cut surface to enable ready joining.

An additional object of the invention is that the ball of the ball retainer be upwardly oriented.

It is again an object of the invention that the ball retainer be constrained against rotation within an anchor.

Yet another object of the invention is that the ball retainer allow pivoting and inclination of the tooth prosthesis on the ball.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein:

FIG. 1 is an exploded, perspective view of the two separate components of the novel ball retainer. The upper component is shown tilted relative to the lower component to reveal the bottom surface of the upper component.

FIG. 2 is a diagrammatic, side elevational view of the invention, showing the novel ball retainer in modified form superimposed over environmental elements. The environmental elements are shown in broken lines.

DETAILED DESCRIPTION OF THE PREFERRED EMBODIMENTS

Shown in its original form in FIG. 1 of the drawings, the novel ball retainer 10 is intended for reproducing therefrom an original for casting a proposed reproduced permanent implant member intended to support a tooth prosthesis on an anchor implant in the jaw of a person, as illustrated in FIG. 2. Ball retainer 10, when modified to suit a particular application and glued or otherwise joined into a single, unified part, will serve as an original for a molding method of reproducing a similar, permanent implant member from a more durable material.

As seen in FIG. 1, ball retainer 10 comprises a prosthesis engagement member 12 and an anchoring member 14. Prosthesis engagement member 12 includes a column 16 of length generally excessive, given typical proportions of implant components. Column 16 has a proximal end 18 to which is fixed a ball 20, and a distal end 22 having a flat bottom surface 24. Flat bottom surface 24 terminates prosthesis engagement member 12, being unencumbered by any attached structure projecting or located below flat bottom surface 24.

Anchoring member 14 has a platform 26 bearing a flat upper surface 28 and a lower surface 30. A keyed shank 32 is fixed to and depends from lower surface 30. Shank 32 is keyed in that it is non-circular in cross section, and thus will be constrained against rotation about its longitudinal axis 34 when placed in a cooperating anchor (see FIG. 2). Upper surface 28 is perpendicular to longitudinal axis 34. Distal end 36 of shank 32 is tapered to facilitate insertion into the opening of the anchor.

Most anchors employed in dental implants conventionally have hexagonal openings for receiving members corresponding to shank 32. Of course, the opening and shank could be of any polygonal, irregular, or curved configuration in order to prevent rotation. As originally provided to dental practitioners, prosthesis engagement member 12 and an anchoring member 14 are separate from and unjoined to one another.

Column 16 has a longitudinal axis 38 to which flat bottom surface 24 is perpendicular. It is not critical to the invention that surface 24 be flat, since it is contemplated that in most installations, this surface 24 will be modified by removal of material to reconfigure prosthesis engagement member 12. However, it is contemplated that initial axial alignment of members 12 and 14 will enable a dental practitioner to readily envision necessary forming of column 16 prior to actually removing material from column 16.

The proposed final member reproduced from ball retainer 10 will be one single, integral part. Therefore, members 12 and 14 must be solidly joined after height and axial alignment are suitable. In order to render height and axial alignment suitable, the dental practitioner planes away material from the bottom of column 16 of member 12. This cut may be parallel to original surface 24, if only height is to be adjusted. Alternatively, and in most cases, the cut is angled, as indicated at 40 in FIG. 2.

FIG. 2 shows ball retainer 10 after being modified to adjust height and axial alignment between members 12 and 14. It will also be understood that the reproduced final member has characteristics of dimension and configuration similar to those shown for ball retainer 10 in the condition depicted in FIG. 2. Ball retainer 10 is modified by assembling it to anchor 2 disposed within tissue 4 of the jaw. Member 14 is inserted into anchor 2 and member 12 is modified until deemed satisfactory for supporting a tooth prosthesis 6 at a height and upright orientation even with those of existing teeth (not shown). When modification to column 16 is completed, member 12 is glued or otherwise adhered at the new lower surface of column 16 to platform 26 of member 14.

Referring again to FIG. 1, to assure strong bonding of member 12 to member 14, a relatively great contact or attachment area is provided. This contact area coincides with upper surface 28 of platform 26. Platform 26 has a cross sectional configuration and a diameter 42 similar to those of column 16. Diameter 42 is greater than diameter 44 of shank 32. Since shank 32 is hexagonal as depicted, it has more than one possible diameter. Diameter 44 is the greatest possible diameter of shank 32. The relatively great proportion of diameter of contact area to ball 20 and shank 32 is desirable since member 12 must be glued to member 14, and a relatively large contact area increases likelihood of a successful bond.

Returning to FIG. 2, it is possible that tooth prosthesis 6 will be pivoted on ball 20. To avoid potential interference between tooth prosthesis 6 and column 16, ball 20 is connected to column 16 by a neck 46. Neck 46 has a diameter 48 of magnitude less than that of column 16. Ball 20 is thereby spaced apart from yet fixed to column 16.

The reproduced final member (not shown) may be inserted into anchor 2 by inserting the shank thereof linearly into the opening of anchor 2. If the shank were threaded, it is possible that ball 20 and, if fitted to the final member, tooth prosthesis 6 would interfere with neighboring teeth (not shown) due to angular misalignment between the column and shank of the final member. This is why shank 32 is keyed rather than threaded.

Members 12 and 14 are fabricated from materials susceptible to molding and casting methods of reproduction. Typically, synthetic resins will be employed as constituent materials. The final member may be cast from a suitable metal, metal alloy, ceramic, or any other suitable material.

It is to be understood that the present invention is not limited to the embodiments described above, but encompasses any and all embodiments within the scope of the following claims.

I claim:

1. A ball retainer for reproducing therefrom a reproduced, permanent implant member intended to support a tooth prosthesis on an anchor implant in the jaw of a person, comprising:

an anchoring member having a platform having a flat upper surface and a lower surface, and a keyed shank fixed to and depending from said lower surface; and a prosthesis engagement member comprising a column having a proximal end and a distal end, and a ball fixed to said proximal end, said distal end of said column having a flat bottom surface terminating said prosthesis engagement member, said anchoring member and said prosthesis engagement member being separate from and unjoined to one another.

2. The ball retainer according to claim 1, said shank having a longitudinal axis and said flat upper surface of said platform of said anchoring member disposed perpendicularly to said longitudinal axis of said shank.

3. The ball retainer according to claim 1, said column having a longitudinal axis and said flat bottom surface disposed perpendicularly to said longitudinal axis of said column.

4. The ball retainer according to claim 1, said platform having a cross sectional configuration and a diameter, and said column having a cross sectional configuration similar to that of said platform and a diameter similar to that of said platform.

5. The ball retainer according to claim 1, said shank having a maximum diameter and said platform having a diameter greater than said maximum diameter of said shank, whereby area of attachment of said prosthesis engagement member to said anchoring member is greater than the cross sectional area of said shank.

6. The ball retainer according to claim 1, said shank having a tapered distal end.

7. The ball retainer according to claim 1, said prosthesis engagement member comprising a neck disposed between, fixed to, and joining said column and said ball, said column having a first diameter, said ball having a second diameter, and said neck having a third diameter less in magnitude than said first diameter and said second diameter, whereby said ball is spaced apart from yet fixed to said column.

8. A ball retainer for reproducing therefrom a reproduced, permanent implant member intended to support a tooth prosthesis on an anchor implant in the jaw of a person, comprising:

an anchoring member having a platform having a flat upper surface and a lower surface, and a keyed shank fixed to and depending from said lower surface, said shank having a longitudinal axis and a tapered distal end, said flat upper surface of said platform of said anchoring member disposed perpendicularly to said longitudinal axis of said shank; and a prosthesis engagement member comprising a column having a longitudinal axis, a proximal end, and a distal end, and a ball fixed to said proximal end, said distal end of said column having a flat bottom surface terminating said prosthesis engagement member, and said flat bottom surface disposed perpendicularly to said longitudinal axis of said column, said prosthesis engagement member comprising a neck disposed between, fixed to, and joining said column and said ball, said column having a first diameter, said ball having a second diameter, and said neck having a third diameter less in magnitude than said first diameter and said second diameter, whereby said ball is spaced apart from yet fixed to said column, said anchoring member and said prosthesis engagement member being separate from and unjoined to one another, said platform having a cross sectional configuration and a diameter, and said column having a cross sectional configuration similar to that of said platform and a diameter similar to that of said platform, whereby said column and said platform may be joined by adhering after said column is planed, and said shank having a maximum diameter and said platform having a diameter greater than said maximum diameter of said shank, whereby area of attachment of said prosthesis engagement member to said anchoring member is greater than the cross sectional area of said shank.

* * * * *